US008278238B2

(12) United States Patent
Johannes et al.

(10) Patent No.: US 8,278,238 B2
(45) Date of Patent: Oct. 2, 2012

(54) TRIPLET EMITTER HAVING CONDENSED FIVE-MEMBERED RINGS

(75) Inventors: Hans-Hermann Johannes, Braunschweig (DE); Wolfgang Kowalsky, Braunschweig (DE); Sven Ammermann, Braunschweig (DE); Michael Kroener, Braunschweig (DE); Ute Jana Weinaug, Braunschweig (DE)

(73) Assignees: Universitaet Bruanschweig, Bruanschweig (DE); BASF Aktiengesellschaft, Ludwigshafen (DE)

( * ) Notice: Subject to any disclaimer, the term of this patent is extended or adjusted under 35 U.S.C. 154(b) by 1055 days.

(21) Appl. No.: 12/066,144

(22) PCT Filed: Sep. 7, 2006

(86) PCT No.: PCT/EP2006/066153
§ 371 (c)(1),
(2), (4) Date: Sep. 12, 2008

(87) PCT Pub. No.: WO2007/028822
PCT Pub. Date: Mar. 15, 2007

(65) Prior Publication Data
US 2009/0165846 A1 Jul. 2, 2009

(30) Foreign Application Priority Data
Sep. 7, 2005 (WO) ............... PCT/EP2005/054431

(51) Int. Cl.
*B01J 31/00* (2006.01)
*H01L 31/00* (2006.01)
(52) U.S. Cl. ......... 502/152; 502/155; 502/167; 136/256
(58) Field of Classification Search ................ 502/152, 502/155, 167; 136/256
See application file for complete search history.

(56) References Cited

U.S. PATENT DOCUMENTS
6,916,554 B2 * 7/2005 Ma et al. ................. 428/690

FOREIGN PATENT DOCUMENTS
| JP | 2001-181616 | * | 7/2001 |
| JP | 2004 319438 | | 11/2004 |
| JP | 2004-319438 | * | 11/2004 |

* cited by examiner

*Primary Examiner* — Ling Choi
*Assistant Examiner* — Monique Peets
(74) *Attorney, Agent, or Firm* — Oblon, Spivak, McClelland, Maier & Neustadt, L.L.P.

(57) ABSTRACT

The present invention relates to light emitting compounds, especially to triplett emitters suitable for electrooptical applications. Compounds according to the invention are organometallic complexes of a metal, preferably Ir, having a backbone of one five-membered ring that is linked to a five- or six-membered ring, by an intermediate six-membered ring. These compounds are suitable for adaptation to the emission of light in the UV to NIR range by adaptation of atoms or groups within at least one of the five-membered or six-membered ring structures.

18 Claims, 7 Drawing Sheets

TRIPLET EMITTER HAVING CONDENSED FIVE-MEMBERED RINGS

The present invention relates to light emitting compounds, especially to phosphorescent compounds useful for electrooptical, e.g. electroluminescent applications. Uses of compounds according to the invention are for example as layer in OLEDs or for laser applications to emit visible light when excited by electric current, as well as forming layers for light absorbtion in photovoltaic devices.

In greater detail, compounds according to the invention are triplett emitters, using the highly effective transformation of electric energy to radiation which occurs in organic compounds complexing a metal atom, preferably Ir.

STATE OF THE ART

One of the first available triplett emitters is tris(2-phenylpyridine)iridium ($Ir(ppy)_3$) (Grushin et al., Chem. Communications 1494-1495 (2001)). In this compound, two six-membered aromatic cycles are connected by one σ-bond, one of which contains a nitrogen atom for complexing the metal atom. The emitter properties of $Ir(ppy)_3$ have been investigated in detail by Finkenzeller et al. (Chemical Physics Letters 377, 299-305 (2003)).

From WO 2004/016711 A1 a large variety of $Ir(ppy)_3$ derivatives is known, provided with substituents having electron drawing or donating groups to influence the emitter properties.

Li et al. (Organometallics 24, 1329-1335 (2005)) describe six-membered Ir complexes for use in electroluminescence, based on an 8-phenylchinoline framework. The iridium (Ir) complexes according to Li et al. are reported to emit light at a wavelength in the range of deep red. One representative of the Ir complexes containing six-membered chelates is bis[8-(3,5-difluorophenyl)-quinoline]iridium(III) acetylacetonate. In these compounds, two aromatic moieties are linked by a σ-bond and form a six-membered cyclic structure when chelating Ir.

JP2004319438 discloses a large variety of structures for emitters, complexing Rh. All of the structures comprise a six-membered ring containing the nitrogen which complexes the Rh.

OBJECTS OF THE INVENTION

The present invention seeks to provide organometallic complexes, suitable for electrooptical applications, i.e. as triplett emitters, having alternative structures to known complexes.

Preferably, the present invention seeks to provide triplett emitters having alternative structures to known electroluminescent compounds, which alternative structures preferably have an improved luminescence yield of the electric energy consumed. More preferably, the compounds of the invention have a high chemical and thermal stability.

GENERAL DESCRIPTION OF THE INVENTION

Figure 1:
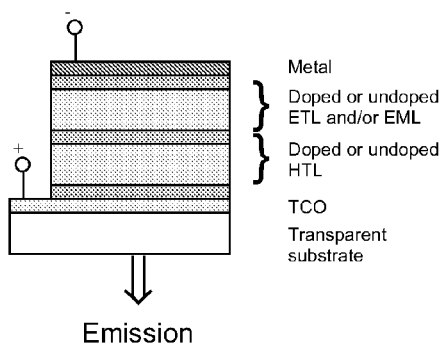
FIG. 1 an OLED in cross-section,
FIG. 2 an inverted OLED in cross-section,
FIG. 3 a further embodiment of an OLED having two adjacent emissive layers in cross-section,
FIG. 4 a solar cell in cross-section,
FIG. 5 an electroluminescence spectrum of a compound according to the invention forming an emissive layer in an OLED,
FIG. 6 the current density over the voltage applied for the OLED used in FIG. 1,
FIG. 7 the luminance over the voltage applied for the OLED used in FIG. 1,
FIG. 8 a plot of the current density over voltage applied for an OLED according to FIG. 3 with $Ir(MNTZ)_3$ as the emitter in a TPBi matrix for different emissive layer thicknesses,
FIG. 9 a plot of the luminescence for the OLEDs used for measurements of FIG. 8,
FIG. 10 a plot of the luminescence efficiency for one of the OLEDs used for measurements of FIG. 8,
FIG. 11 a plot of the long-term stability for one of the OLEDs used for measurements of FIG. 8,
FIG. 12 an electroluminescence spectrum of $1r(MNTZ)_3$,
FIG. 13 a DSC of $1r(MNTZ)_3$,
FIG. 14 an HPLC chromatogram of $1r(MNTZ)_3$, and
FIGS. 15 and 16 emission spectra of compounds according to the invention.

The present invention relates to compounds suitable for electrooptical applications, especially to triplett emitters. In general, the following arrangement of layers needs to be present in an OLED comprising an inventive emitter compound: an anode, e.g. a transparent conductive metal oxide (TCO)-covered substrate like a ZnO, preferably an ITO (indium tin oxide)-covered glass or organic transparent sheet material, a hole transporting material, an emissive layer, optionally a hole blocking material and/or an electron transporting material, and an electrically conductive cathode layer.

The emitter compounds according to the invention are suitable for adaptation to the emission of light in the UV, visible and NIR, preferably in the visible range by variation of atoms, e.g the replacement of carbon for a heteroatom, or groups within the five-membered nitrogen containing ring complexing the metal atom or within the five- or six-membered ring containing the carbon atom complexing the metal atom. In the alternative to introducing a heteroatom in the place of a carbon atom, the wavelength of emitted light can be influenced in a predictable way by substituting the carbon and/or heteroatoms within the structure complexing the metal atom.

Compounds according to the invention are organometallic complexes of a transitional metal, e.g. selected from Os, Pt and Re, Ru, Pd, preferably Ir. The transition metal atom is complexed by one nitrogen atom and one carbon atom contained in the organic backbone, forming a five-membered ring structure including the metal atom.

The aromatic backbone structure provides the organic portion of the emitter compound and comprises two cyclic structures, B and C, connected to one another by two linkages that are formed by an intermediate linker aromatic group (A), which is a six-membered ring. The linker group A arranged between cyclic structures B and C shares atoms with cyclic structures B and C, respectively. One of these cyclic structures, cyclic structure B, contains a nitrogen to form a linkage to the complexed metal atom, the other, cyclic structure C, contains a carbon atom to form a linkage to the metal atom.

Cyclic structure B is a five-membered ring. Cyclic structure C independently is a five- or six-membered ring.

Preferably, cyclic structures B and C contain unsaturated bonds, preferably at least two conjugated unsaturated bonds, most preferably, structures B and C are aromatic.

Cyclic structure A is aromatic, forming a six-membered ring sharing atoms with adjacent cyclic structures B and C.

Optionally, also cyclic structures B and/or C contain additional hetero-atoms, e.g. selected from N, O, S, Se, Te and Si.

The metal atom is selected from Pt, Pd, Ru, Re, Os, preferably Ir.

For saturation of the valences of the metal atom, more than one ligand, e.g. 2 or 3, may form five-membered ring structures with the metal atom each, or, alternatively, saturation may be provided by ancillary coordinating ligands, such as compounds containing the acetylacetonate group, the picolinate group, the 2-pyridylformiate group, the 2-(4H-[1,2,4]triazol-3-yl)pyridine group, and/or the dipivaloylmethanate group.

Generally, the metalchelate complexes according to the present invention can be represented by general formula I:

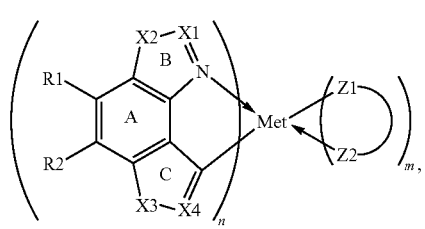

I wherein cycle B is a five-membered ring, cycle A is a six-membered ring, and cycle C can be a six-membered or a five-membered ring, X1 is selected from CR' and N,
X2 is selected from NR', O, S, Se, Te, CR'R", and SiR'R",
X3, X4=N, NR', S, O, CR', CR'R", CR'=CR", N=N, CR'=N, N=CR", SiR', SiR'R", Se, Te,
with R', R" selected from A1, CN, NA1A2, OA1, SA1, F, Cl, Br, I, CNO, NCO, CA1O, COOA1, wherein A1, A2 is any substituted (hetero)alkyl, (hetero)aryl, optionally carrying polymerizable groups, e.g. aldehyde, alcohol, cyanato, isocyanato, an at least mono-unsaturated olefinic group, vinyl, alkylidene, allyl, oxethane, acryl, amine, oxirane, carbonic acid or ester groups, or H,
Met is selected from Ir, Pt, Ru, Re, Pd and Os,
n=1 to 3, m=3−n for Met=Ir, Os, Ru, Re und n=1 to 2, m=2-n for Met=Pt, Pd
R1, R2 are independently selected from A1, CN, NA1A2, OA1, SA1, F, Cl, Br, I, CNO, NCO, CA1O, COOA1, wherein A1, A2 is any substituted (hetero)alkyl, (hetero)aryl, optionally carrying polymerizable groups, e.g. aldehyde, alcohol, cyanato, isocyanato, an at least mono-unsaturated olefinic group, vinyl, alkylidene, allyl, oxethane, acryl, amine, oxirane, carbonic acid or ester groups, or H, wherein R1 and R2 can be substituted and/or can be linked to each other, forming an anellated substituent to cyclic structure A, B and C, preferably condensed moieties, and
wherein Z1 and Z2 are part of an ancillary saturating ligand.

According to a preferred embodiment, polymerizable groups linked to cyclic structure A, B and/or C serve to provide linkages of the metal-complexing emitter moiety to at least one polymeric group. The polymeric group can function as a matrix compound and can e.g. be selected from an inert group, an electron transporting group and/or a hole transporting group. As used for the purposes of this invention, the term "inert group" refers to groups that are not conductive, i.e. do not provide charge transport under the electric conditions used in electrooptic devices according to the invention, and, accordingly are herein not comprised in the groups of hole or electron transporting groups. Examples for inert groups may be chosen among polyalkylenes like polyethylene, polypropylene, and polystyrene, polymethacrylates, polyurethanes, derivatives of these groups as well as copolymers thereof.

The saturating ligand

forms a bidentate ligand to the complexed metal atom and is a monoanionic ligand, wherein Z1 and Z2 independently represent atoms, which are optionally substituted and linked by a chemical bond or by an intermediary group that arrange one, two or three additional atoms between Z1 and Z2. Preferably, both Z1 and Z2 as well as intermediary groups between these are substituted with polymerizable groups to provide a linkage with at least one polymeric group.

Intermediary groups can be selected from groups listed for Z1. Z1 and Z2 are for example selected independently from methylene, substituted methylene, N, NR1, S, O, Se, Te, CR1, SiR1, CR1R2, SiR1R2, CR2=CR3, N=N, CR1=N, with R1 to R3 independently selected from A1, CN, NA1A2, OA1, SA1, F, Cl, Br, I, $SO_2A1$, CNO, NCO, CA1O, COOA1 wherein A1 and A2 is any substituted (hetero)alkyl, (hetero)aryl, optionally carrying a polymerizable group, or H.

Preferably, the saturating ligand is selected from the group comprising acetylacetonate, 2-pyridylacetate (also termed picolinate), dipivaloylmethanate, 2-pyridylformiate, 2-(4H-[1,2,4]triazol-3-yl)pyridine as a subunit. In this respect, the term subunit refers to the specific groups mentioned and compounds comprising these groups, which carry additional substituents as well as derivatives thereof, e.g. substituted with polymerizable groups linking polymeric groups, and to groups which comprise the general structure indicated above and saturate free valences of the metal atom which is otherwise complexed by the emitter moiety containing ring structures A, B and C. In the formulae and compounds according to the invention, saturating ligands of specified and exemplary compounds can be exchanged for one another, even if one specific saturating ligand is indicated.

In a preferred embodiment, the saturating ligand is substituted with at least one polymeric group, e.g. selected from an inert group, an electron transporting group and/or a hole transporting group. Linkage to the at least one polymeric group is obtained by polymerizable groups substituting the saturating ligand for providing connecting bonds. Substitution of the saturating ligand with a polymeric group is independent from the substitution of the cyclic structure A, B and/or C with a polymeric group. Accordingly, in a further embodiment, both at least one of cyclic structures A, B and/or C and the saturating ligand are linked to a polymeric group. Substitution of the saturating ligand and/or of the emitter moiety complexing the metal atom with polymeric groups can be used for generating molecules characterized as dendrimers, oligomers or polymers. As a specific advantage of substitution with polymeric groups, compounds are obtained that have triplett emitter moieties, equipped with the properties conferred by the substituent, which are further suitable for coating from solution, e.g. by spin coating, spray coating, or even jet-printing.

The π-bonds contained in cyclic structures B and C represented in general formula I can differ, depending on heteroatoms in cycles B and/or C, and depending on cycle C being a five- or six-membered ring. However, the skilled person can easily determine, which bonds formally are π-bonds.

Cyclic structures B and C are independently non-aromatic, non-conjugatedly or conjugatedly aromatic rings. Preferably, aromatic structure A connects cyclic structures B and C, forming a condensed system comprising cyclic structures A, B and C.

With cyclic structure A being aromatic, cyclic structures B and C are anellated by intermediate aromatic cyclic structure A, wherein cyclic structures B and C can be saturated or partially unsaturated cyclic, preferably conjugatedly aromatic.

Accordingly, it is a specific advantage of the compounds of the present invention that cyclic structure A connects cyclic structures B and C in a way that restricts rotation around the bond linking cycles B and C, which results in a fixed conformation of cyclic structures B and C in respect to each other. In the preferred embodiment, cyclic structures A, B and C form a conjugated system, creating an essentially planar conformation of the backbone structure.

Therefore, triplett emitters according to the present invention avoid energy dissipation which would be caused by rotational movements of groups, which would result in radiationless deactivation, i.e. thermal relaxation processes instead of emitting light. As a result, triplett emitters according to the present invention have a better yield in light emitted, i.e. a more effective generation of electroluminescence in relation to electric energy consumed.

A specific advantage of the compounds according to the invention over e.g. compounds having a six-membered ring as cycle B containing the metal-complexing nitrogen is based on cyclic structure B being a five-membered ring. The advantages are firstly that a five-membered anellated ring can generally be generated by less complex and/or more efficient synthesis routes. Secondly, the electron density can be tuned and adjusted from electron rich to electron poor or vice versa by replacing carbon atoms of the ring with hetero atoms, resulting inter alia in a change of the emission wavelength and/or a change of the electron or hole transporting properties. Accordingly, these effects can be achieved at least in part without introducing substituents to the ring structure, or reducing the requirement for the number and/or size, e.g. higher electron density, of substituents, e.g. in comparison to six-membered rings, which require more substituents to yield the same effects for the emitter complex. In addition, the larger number of substituents normally leads to a reduction of the emission efficiency because of energetic losses due to vibrational energy conversion instead of radiation are increased. Further, a reduced number and/or reduced size of substituents often results in increased glass-transition temperatures, i.e. higher temperature stability.

Optionally, compounds according to the invention are chemically linked to substituent groups, e.g. substituent polymeric groups, i.e. ring structures A, B and/or C may independently carry substituents to their carbon or hetero atoms which do not participate in linkages between these ring structures or in forming the metal complex. Substituents may be selected from (hetero-)alkyl, (hetero-)aryl, —NR1$_2$, —OR1, —SR1, —CN, —F, —CF$_3$, with R1 independently selected from A1, CN, NA1A2, OA1, SA1, F, Cl, Br, I, SO$_2$A1, CNO, NCO, CA1O, COOA1 wherein A1 and A2 is any substituted (hetero)alkyl, (hetero)aryl, optionally carrying polymerizable groups, e.g. aldehyde, alcohol, cyanato, isocyanato, an at least mono-unsaturated olefinic group, vinyl, alkylidene, allyl, oxethane, acryl, amine, oxirane, carbonic acid or ester groups, or H, and electrooptically functional groups, wherein two or more substituents can be condensed arenyl groups or groups forming a higher condensed matrix materials, e.g. selected from an inert group, an electron transporting group and/or a hole transporting group. As a consequence of the emitter compound according to the invention being linked with charge transporting groups, the layer structure of an electrooptic device can be simplified by omitting the respective charge transport layer. In detail, an emitter compound linked with electron transporting groups can be used in an electrooptic device having a layer structure without electron transporting layer, and an emitter compound linked with hole transporting groups can be used in an electrooptic device having a layer structure without hole transporting layer.

In one embodiment, compounds according to the invention are substituted with polymeric groups, wherein at least one of the ring structures A, B and/or C is provided with a polymerisable group, forming a linkage to the polymeric group. In addition or in alternative to substitution of at least one of the ring structures, the saturating ligand can be substituted with one or more polymerisable groups for forming a bond to a polymeric group.

Polymerisable groups can e.g. be formed by an aldehyde, alcohol, cyanato, isocyanato, an at least mono-unsaturated olefinic group, e.g. vinyl, alkylidene, allyl, or an oxethane, acryl, amine, oxirane, carbonic acid or ester group. In this embodiment, the polymeric group linked to the polymerisable group can be an inert group, an electron transporting group and/or a hole transporting group. In this embodiment, it is preferred that the polymeric group is further connected to the saturating ligand.

Further, two or more identical or differing molecules of the emitter compounds according to the invention can be linked to a polymeric group, independently by linkage to one of cyclic structures A, B or C, and, alternatively or additionally by linkage to the saturating ligand. In this embodiment, a dendrimer, oligomer or polymer is formed, comprising at least two or more molecules of the emitter compounds according to the invention, linked to one polymeric group. Independent from linkage of two or more emitter compounds to a common polymeric group, the emitter compounds can optionally be substituted by one or more identical or differing polymeric groups, which optionally may provide electric functions, e.g. which are selected independently from inert groups, electron transporting groups and/or hole transporting groups.

Further, substituents to cyclic structures A, B and C can form aromatic substructures, e.g. aromatic residue with or without conjugation to cyclic structures A, B and/or C and preferably result in a higher condensed system, comprising cyclic structures A, B and C.

It is a specific advantage of the compounds according to the present invention that the wavelengths of light emitted, i.e. the colour of light emitted under excitation can be influenced easily by alteration of atoms or groups R1, R2, X1, X2, X3 and/or X4. For example, a shift of the dipole moment of the compound by variation of one of R1, R2, and X1 to X4 directly influences the range of wavelengths emitted.

Shifting of the wavelength maximum can preferably be achieved across the range of UV or visible to NIR wavelengths. According to the preferred embodiment, the shifting of wavelengths is especially pronounced for cyclic structures B and C being conjugatedly aromatic, more preferably cyclic structures A, B and C forming a conjugated system.

The electrical, optical, physical, thermal and chemical properties of triplett emitters can further be adapted to desired properties by selecting substituents to cyclic structures B and C as well as to aromatic structure A. Ring structures B and C are derivatized by substituents X1, X2 and X3, X4, respectively. Examples for substituents to any of cyclic structures A, B and/or C, e.g. R1 to R5 of structure II, for influencing the emitter wavelength preferably are selected from charge transporting groups, e.g. selected from electron transporting moieties and hole transporting moieties.

Examples for electron transporting materials and groups are 4,7-diphenyl-1,10-phenanthroline (Bphen) and derivatives thereof like 2,9-dimethyl-4,7-diphenyl-1,10-phenanthroline (BCP), 2,5-diaryloxadiazoles and derivatives thereof like 2-(p-tert.-butylphenyl)-5-(p-biphenyl)-oxadiazole (PBD), oligo-(benzoxadiazol-2-yl)-arenes and derivatives thereof like bis-2,5-(5-tert.-butyl-benzoxadizol-2-yl)-thiophene (BBOT), 1,3-bis[5-(aryl)-1,3,4-oxadiazol-2-yl]benzenes and derivatives thereof like 1,3-bis[5-(p-tert.-butylphenyl)-1,3,4-oxadiazol-2-yl]benzene (OXD-7), 2,5-diaryltriazoles and derivatives thereof like 2-(p-tert.-butylphenyl)-5-(p-biphenyl)-triazole (TAZ), and 2,2',2"-(1,3,5-phenylene)-tris(1-phenylbenzimidazole) (TPBI).

Examples for hole transporting materials and groups are poly(9-vinyl carbazole), tris-[(N,N-diaryl)amino]-triphenylamines like 4,4',4"-tris[(N-(1-naphthyl)-N-phenylaminotriphenylamine] (1-TNATA) and its derivatives, 4,4',4"-tris[(N-(2-naphthyl)-N-phenylamino)-triphenylamine] (2-TNATA) or 4,4',4"-tris[(N-(3-methylphenyl)-N-phenylamino)-triphenyl-amine] (m-TDATA) and its derivatives, 4,4',4"-tris(carbazole-9-yl)triphenylamine (TCTA); N,N,N',N'-tetra-arylbenzidines as N,N,N',N'-tetraphenylbenzidine and its derivatives, N,N'-bis(1-naphthyl)-N,N'-diphenylbenzidine (α-NPD), N,N'-di(naphthalene-2-yl)-N,N'-diphenylbenzidine (β-NPD), 4,4'-bis(carbazole-9-yl)biphenyl (CBP) and its derivatives, and their heteroatom substituted analogs (e.g. thienyl-, selenyl-, furanyl-derivatives); 4,4'-bis(2,2'-diphenylvinyl)-1,1'-biphenyl (DPVBI); triarylamines and their derivatives, 4,4'-bis(N,N-diarylamino)-terphenyls, 4,4'-bis(N,N-diarylamino)-quarterphenyls and their homologs and derivatives, N,N'-dimethylchinacridone and its derivatives, 1,1-bis-(4-bis(4-methyl-phenyl)-aminophenyl)-cyclohexane (TPAC) and N,N',N'-tetraaryldiaminofluorenes as well as their derivatives.

DETAILED DESCRIPTION OF THE INVENTION

Embodiments of general formula I are compounds according to formula II below:

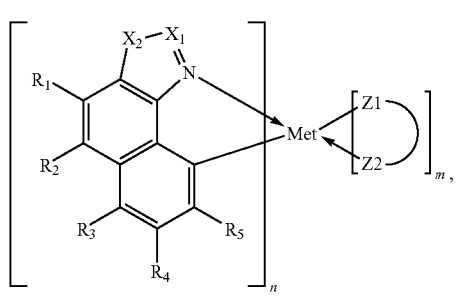

II wherein substituents are defined as given for formula I and substituents R3 to R5 are selected from the groups defined for R1 and/or R2.

More specific embodiments of the compounds according to formula I are given below, wherein the variation of the ancillary saturating ligand is demonstrated on one exemplary ligand:

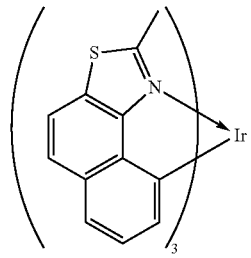

Tris(2-methylnaphth[1,2-d]thiazole)-
iridium(III)

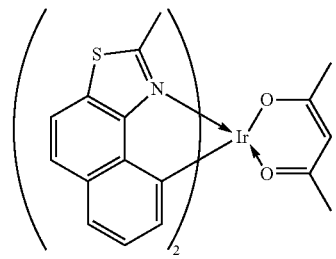

Bis(2-methylnaphth[1,2-d]thiazole)-
iridium(III)acetylacetonate

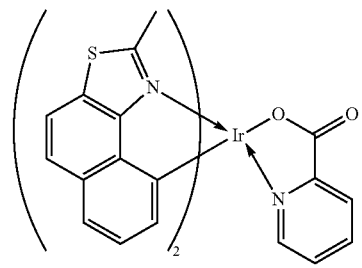

Bis(2-methylnaphth[1,2-d]thiazole)-
iridium(III)-(2-pyridyl)formiate

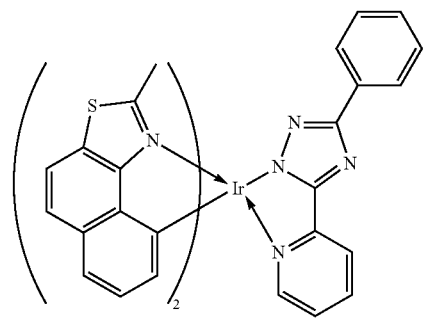

Bis(2-methylnaphth[1,2-d]thiazole)-
iridium-(III)-2-(5-phenyl-2H-[1,2,4]triazol-
3-yl)pyridine wherein ring structure B is varied:

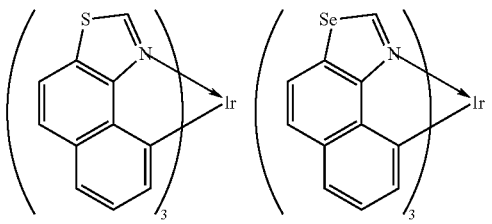

Tris(naphtho[1,2-d]-thiazole)iridium(III)

Tris(naphtho[1,2-d]-selenazole)iridium(III)

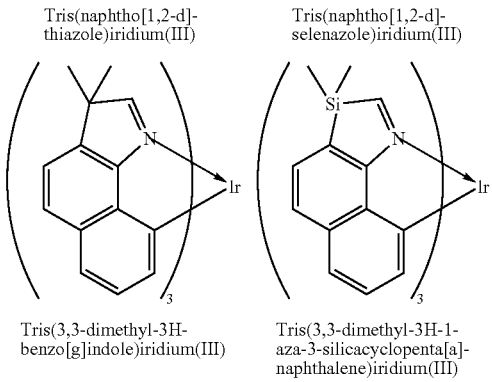

Tris(3,3-dimethyl-3H-benzo[g]indole)iridium(III)

Tris(3,3-dimethyl-3H-1-aza-3-silacyclopenta[a]-naphthalene)iridium(III)

wherein a condensed system of ring structures A, B and C is formed with further anellated substituents:

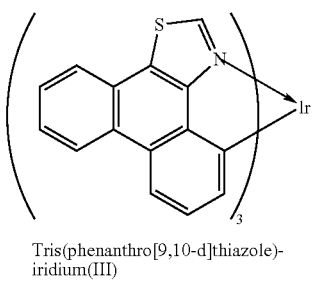

Tris(phenanthro[9,10-d]thiazole)-iridium(III)

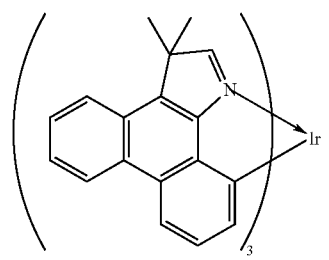

Tris(3,3-dimethyl-3H-dibenzo[e,g]indole)-iridium(III)

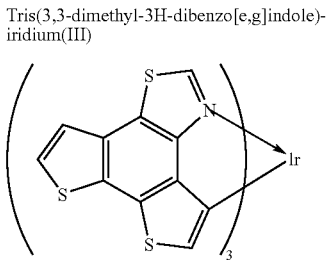

Tris(1,6,7-trithia-3-aza-triindene)-iridium(III)

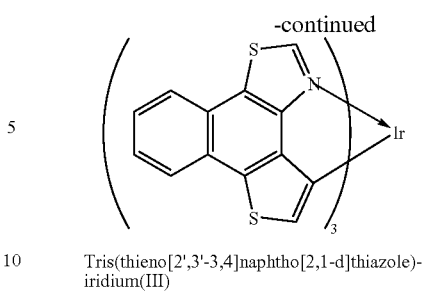

Tris(thieno[2',3'-3,4]naphtho[2,1-d]thiazole)-iridium(III)

Examples for electrooptical devices comprising the compounds according to the invention are schematically depicted in the accompanying figures.

Figure 2:
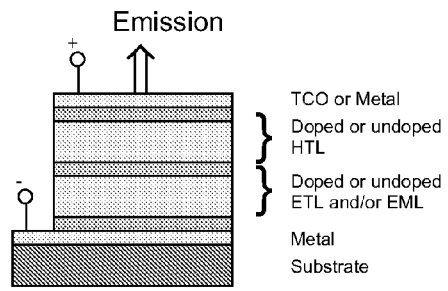
Figure 3:
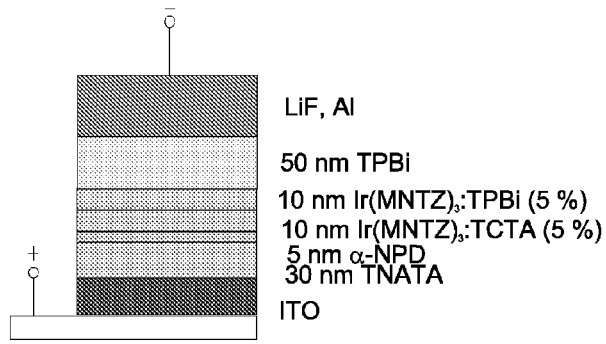

In the OLEDs of FIGS. 1 to 3, the emissive layer is arranged between the electron transport layer (ETL) and the hole transport layer (HTL), which allow for charge transport from and to the emissive layer. In the OLED of FIG. 3, the emissive layer is formed of two adjacent layers comprising an emitter, e.g. Ir(MNTZ)$_3$ of example 1 in different matrix compounds, e.g. at 10% w/w in TPBI and TCTA, respectively.

Figure 4:
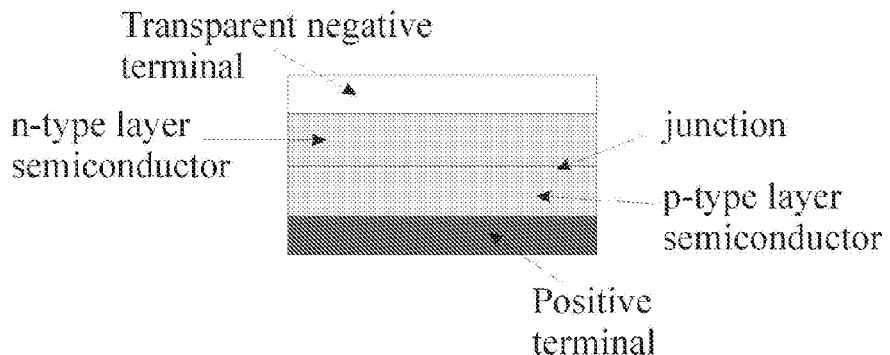

For the solar cell, the compounds of the invention are arranged between the n-type layer semiconductor and the p-type layer semiconductor, indicated in FIG. 4 as "junction". Therein, the semiconductor layers function as transport media for electric charges generated by the compound of the invention from the conversion of incident light.

EXAMPLE 1

Synthesis of
tris(2-methylnaphth[1,2-d]thiazole)iridium(III)
(Ir(MNTZ)$_3$)

Di-μ-chlorotetrakis(2-methylnaphth[1,2-d]thiazole)di-iridium(III) that was produced following Sprouse et al. (J. Am. Chem. Soc. 106, 6647-6653 (1984)) was reacted with the silver salt of trifluoro acetic acid according to M. G. Colombo et al. (Inorg. Chem. 33, 545-550 (1994)).

In detail, iridium (III) chloride hydrate (4.0 g, 0.011 mol) and 2-methylnaphth[1,2-d]thiazole (5.6 g, 0.028 mol) were suspended in 2-ethoxyethanol (138 mL) and water (46 mL) and stirred under an inert gas atmosphere for 68 hours at 130° C. The reaction solution is filtered off and washed with n-hexane and diethylether. The product is a yellow, fine powdery solid (61% yield).

Under an inert gas atmosphere, di-μ-chlorotetrakis(2-methylnaphth[1,2-d]thiazole)di-iridium(III) (500 mg, 0.4 mmol) was stirred for 75 hours at 120° C. with 2-methylnaphth[1,2-d]thiazole (319 mg, 1.6 mmol) and with the silver salt of trifluoro acetic acid (177 mg, 0.8 mmol). The solid is isolated and washed with ethanol. After purification by column chromatography using dichloromethane as the eluent and recrystallization from methanol, a white yellowish powder is obtained (18% yield).

The following characteristics were determined:

$^1$H NMR ([D$_6$]-DMSO): δ=7.88 (d, 1H), 7.78 (d, 1H), 7.35 (d, 1H), 6.91 (m, 1H), 6.34 (d, 1H), 2.15 (s, 3H).

$^{13}$C NMR ([D$_6$]-DMSO): δ=168.5 (s), 157.5 (s), 143.3 (s), 138.4 (s), 131.4 (d), 130.3 (s), 127.1 (d), 126.1 (d), 124.8 (s), 117.9 (d), 117.8 (d), 16.6 (q).

MS (EI): m/z (%): 787 (100) [M]$^+$.

UV/Vis (CH$_2$Cl$_2$): λ/nm (ε)=341 (16 900), 278 (41 000), 230 (106 000). C$_{36}$H$_{30}$IrN$_3$O$_3$ (744.86) calculated: C 54.94 H 3.07 N 5.34 determined: C 54.61 H 3.17 N 5.31.

A general reaction scheme is given below:

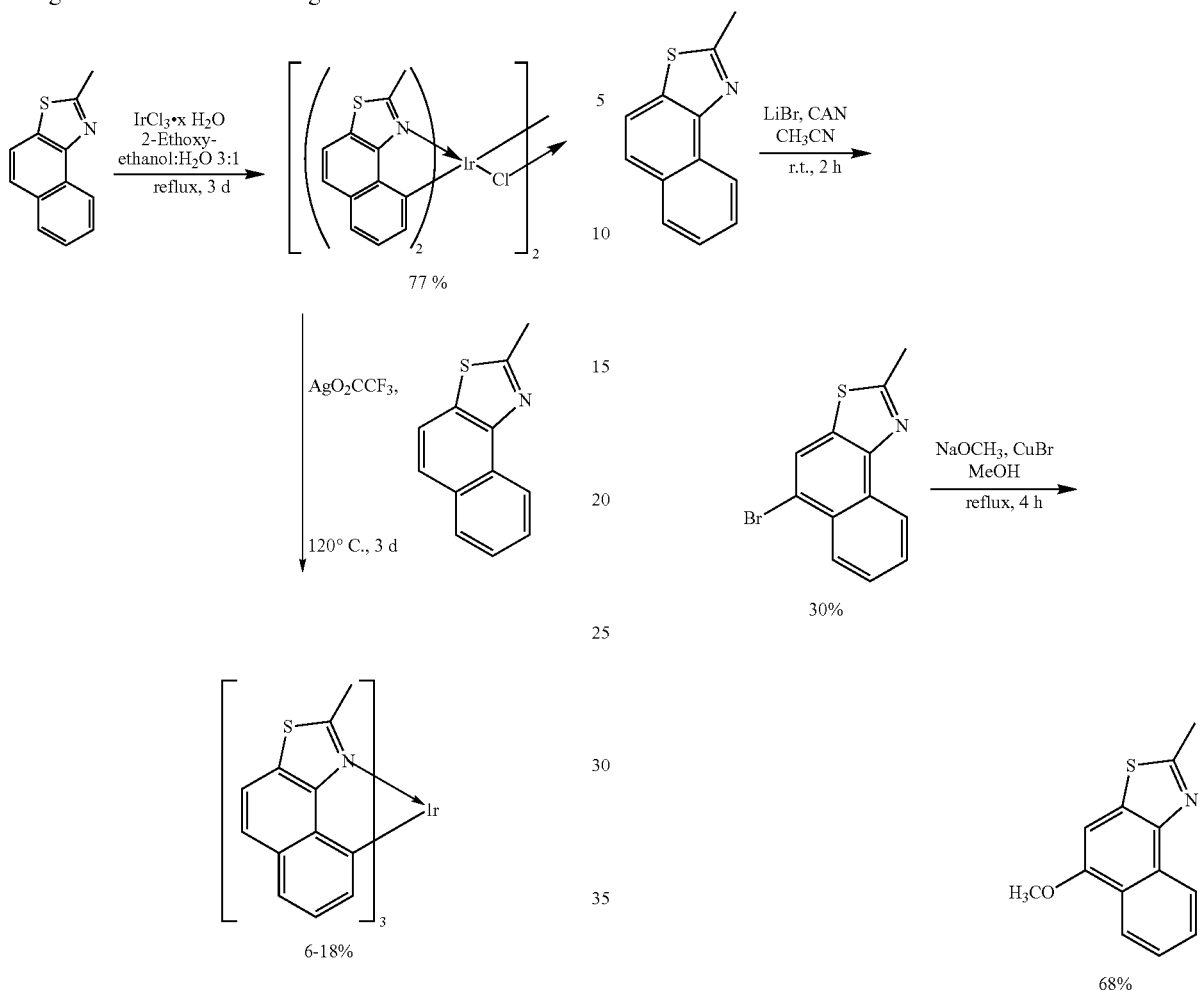

EXAMPLE 2

Synthesis of Methoxylated Ir(OMe-MNTZ)$_3$

For introduction of a methoxy substituent to ring structure A, 2-methylnaphth[1,2-d]thiazol (1 g, 5.02 mmol) and LiBr (0.479 g, 5.52 mmol) were suspended in 10 mL water-free acetonitrile. CAN ((NH$_4$)$_2$Ce(NO$_3$)$_6$, 3.026 g, 5.52 mmol) suspended in acetonitrile was added dropwise and stirred under a nitrogen atmosphere for 1 h at room temperature (according to Subhas Chandra Roy et al., Tetrahedron Lett. 42, 6941 (2001)). Aqueous purification and column chromatography using dichloromethane yields a light yellow solid (30% yield, 0.436 g, 1.57 mmol). The product (300 mg, 1.078 mmol) was then warmed with sodium methylate (582 mg, 10.78 mmol) in methanol (2 mL) (according to H. L. Aalten Tetrahedron 45(17), 5565 (1989)). CuBr (15 mg, 0.108 mmol) was added to the hot solution and refluxed for 4 h. Aqueous purification and column chromatography (dichloromethane/acetic acid ethyl ester 10:1) yields a white solid (68% yield, 168 mg, 0.732 mmol). Complexing with Ir is analogous to Ir(MNTZ)$_3$ according the following reaction scheme:

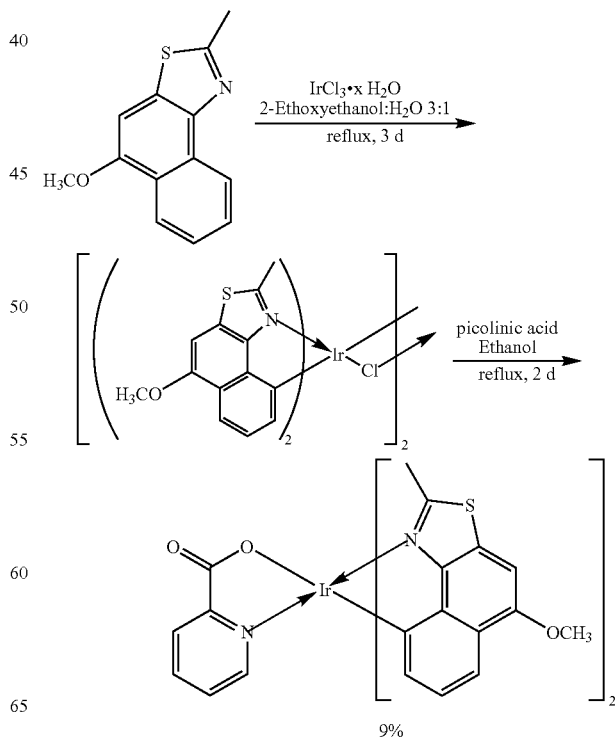

EXAMPLE 3

Synthesis of a Cyano-Substituted Derivative (Ir(cyanoMNTZ)₃)

For introduction of a nitrilo substituent to ring structure A, the following reaction scheme was used:

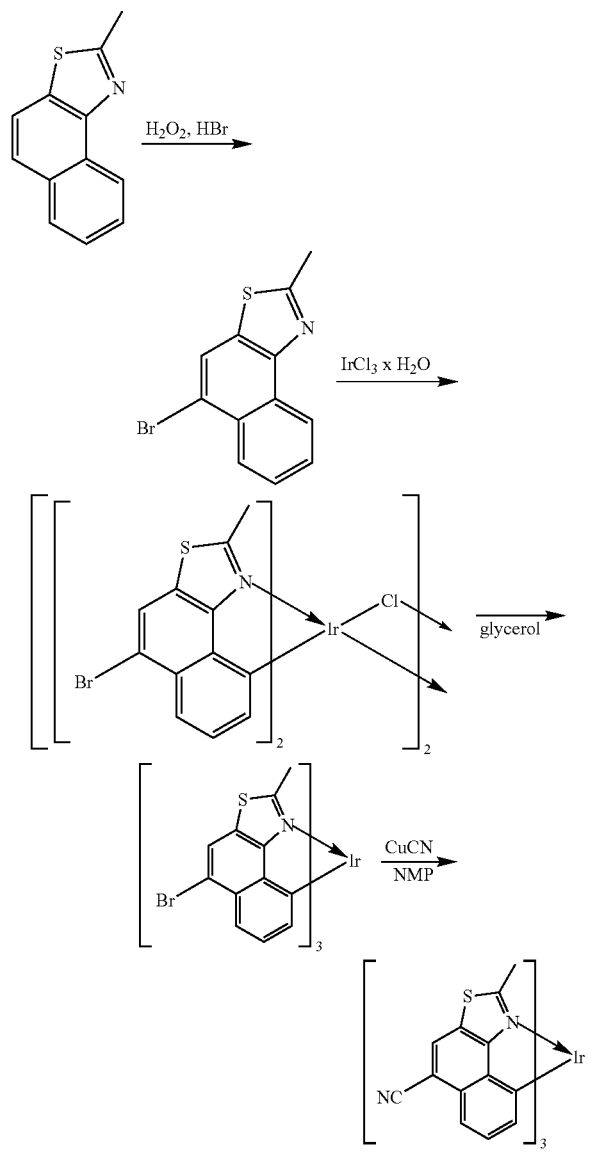

EXAMPLE 4

Synthesis of bis(2-methylnaphth[1,2-d]thiazole)iridium(III)-(2-pyridyl)formiate((MNTZ)₂Irpic)

Under an inert gas atmosphere, di-μ-chlorotetrakis(2-methylnaphth[1,2-d]thiazole)di-iridium(III) (300 mg, 0.24 mmol) and pyridine-2-carboxylic acid (74 mg, 0.6 mmol) were suspended in ethanol. After the addition of a base, the reaction mixture is stirred under reflux for 50 hours. After the addition of water (15 mL), a fine grey greenish precipitate is isolated, purified by column chromatography using dichloromethane/acetone as the eluent and recrystallized from methanol to give a yellow brownish solid (23% yield).

The following characteristics were determined:

$^1$H NMR ([D$_6$]-DMSO): δ=8.10 (m, 2H), 7.95 (m, 2H), 7.77 (m, 3H), 7.51 (m, 1H), 7.37 (m, 2H), 6.96 (m, 2H), 6.29 (d, 1H), 6.11 (d, 1H), 2.99 (s, 3H), 2.11 (s, 3H).

MS (EI): m/z (%): 711 (100) [M]$^+$.

A general reaction scheme is given below:

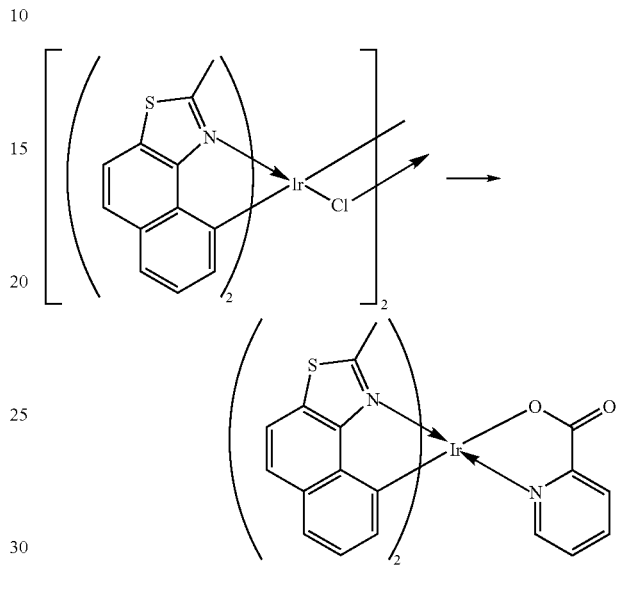

EXAMPLE 5

Synthesis of bis(2-methylnaphth[1,2-d]thiazole)iridium(III)-2-(5-phenyl-2H-[1,2,4]triazol-3-yl)pyridine ((MNTZ)₂IrTriazole)

Following P. Coppo et. al. (Chem. Comm. 1774-1774 (2004)) di-μ-chlorotetrakis(2-methylnaphth[1,2-d]thiazole)di-iridium(III) is reacted with 2-(5-phenyl-2H-[1,2,4]triazol-3-yl)pyridine.

In detail, di-μ-chlorotetrakis(2-methylnaphth[1,2-d]thiazole)di-iridium(III) (300 mg, 0.24 mmol) and 2-(5-phenyl-2H-[1,2,4]triazol-3-yl)pyridine (136 mg, 0.60 mmol) are suspended in dichloromethane (6.6 mL) and ethanol (2 mL) under an inertgas atmosphere. After the addition of a base, the mixture is stirred at room temperature for 41 h. The isolated raw product is purified by column chromatography using dichloromethane/acetone as the eluent, giving a yellow solid (10% yield). A mass of m/z (%)=810 (22) [M]$^+$ was determined by MS (EI). A general reaction scheme is given below:

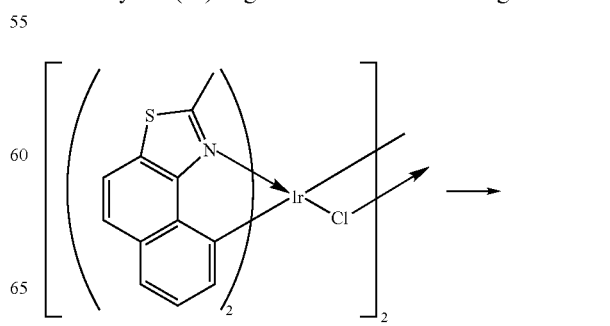

-continued

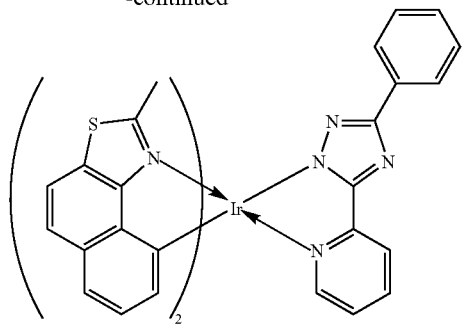

EXAMPLE 4

OLED Comprising tris(2-methylnaphth[1,2-d]thiazole)iridium(III) as the Emissive Layer As an example for an electroluminescent device comprising a compound according to the invention, an OLED having tris(2-methylnaphth[1,2-d]thiazole)iridium(III) in admixture with PVK (poly(9-vinyl carbazole)) as a matrix material as the emissive layer was created by deposition from solution. The OLED consisted of an anode of ITO covered glass, poly(3,4-ethylene dioxythiophene-poly(styrenesulfonate) (PEDOT/PSS) as the hole transporting material, the emissive layer, 2,9-dimethyl-4,7-diphenyl-1,10-phenanthroline (BCP) as the electron transporting layer and/or hole blocking layer, and a LiF/Al cathode layer.

Figure 5:
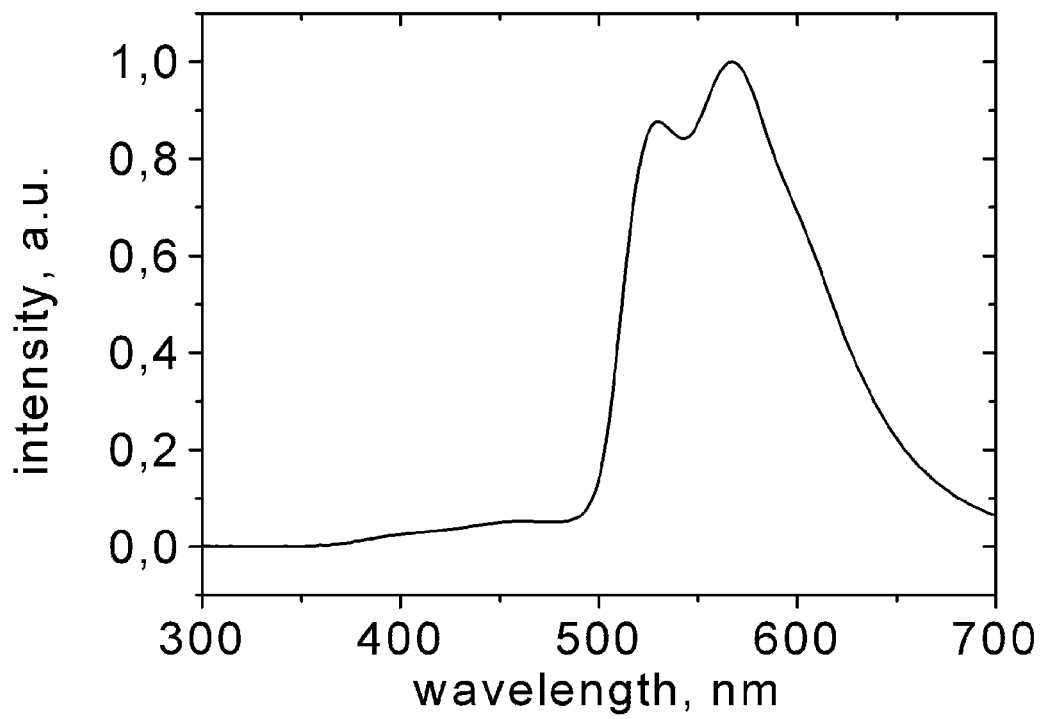
Figure 6:
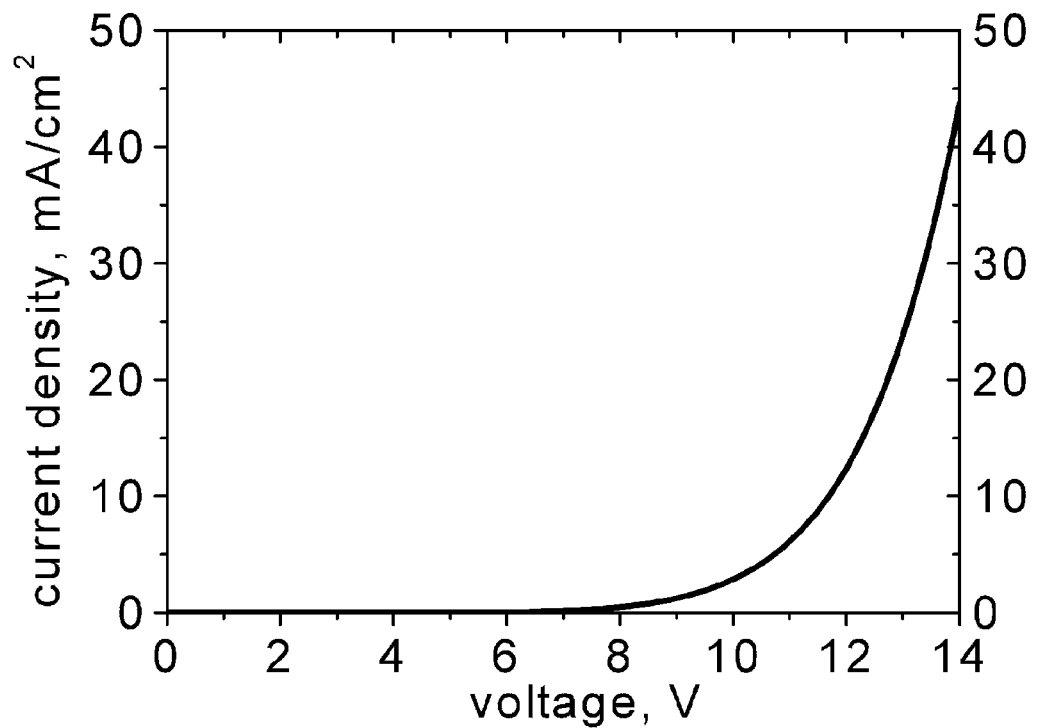
Figure 7:
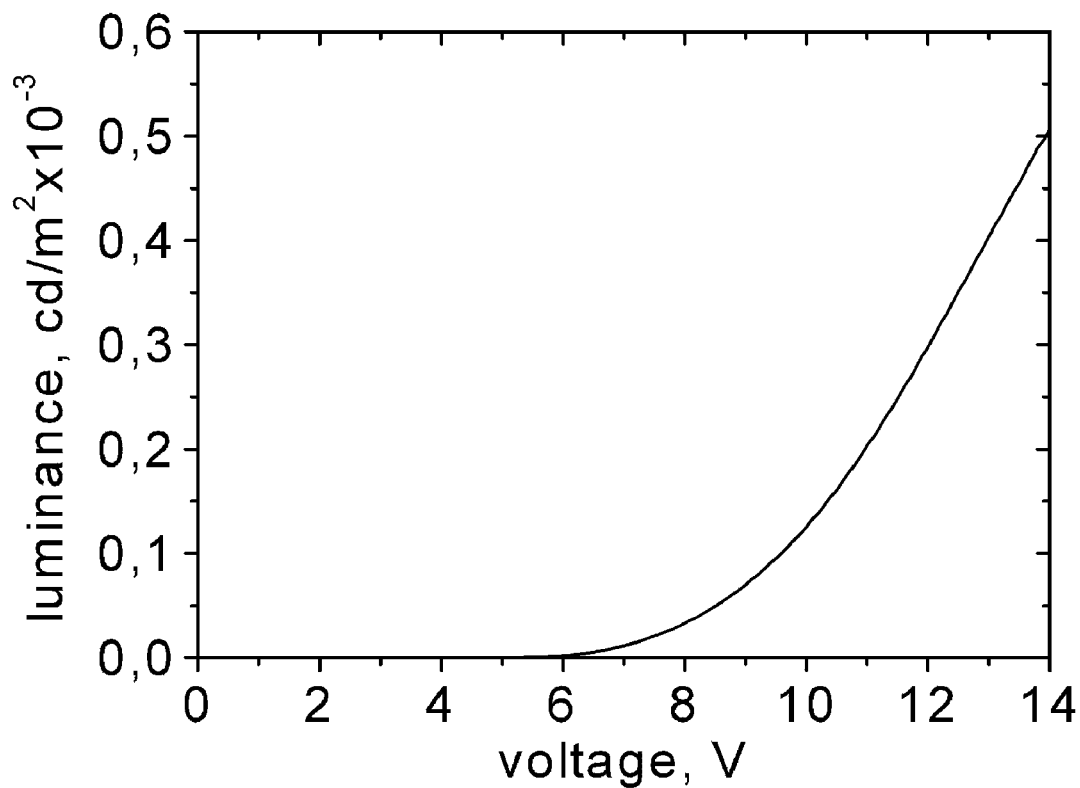

When current was applied, the optical and electrical responses depicted in FIGS. 4 to 6, respectively, were obtained. The normalized luminescence intensity is given in FIG. 4 in arbitrary units (a.u.), showing emission between approx. 500 nm and approx. 650 nm. Current density in response to applied voltage is shown in FIG. 5. FIG. 6 shows the luminance in absolute values in response to applied voltage.

The triplett emitter properties of further compounds according to the invention and their suitability for forming emissive layers could also be demonstrated in OLEDs as representatives for electroluminescent devices.

The following exemplary compounds demonstrate the wavelength emitted can be varied by introduction of small substituents to one of the rings in small numbers, e.g. only one substituent to the core compound comprising cycles A, B and C:

TABLE 1

Estimated emission wavelength of complexes of compounds according to structure I with ring A being mono-substituted:

| Structure | Isomer | Emission [nm] |
|---|---|---|
|  | fac | 541-545 |
|  | fac | 530-534 |
|  | fac | 535-539 |
|  | fac | 597-601 |

TABLE 2

Estimated emission wavelength of heteroleptic complexes of compounds according to structure I:

| Structure | Isomer | Emission [nm] |
|---|---|---|
| 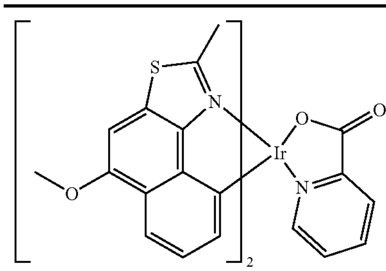 | pseudo fac | 524-529 |
| 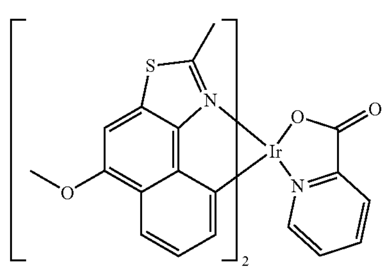 | pseudo mer | 550-556 |

TABLE 2-continued

Estimated emission wavelength of heteroleptic complexes of compounds according to structure I:

| Structure | Isomer | Emission [nm] |
|---|---|---|
| 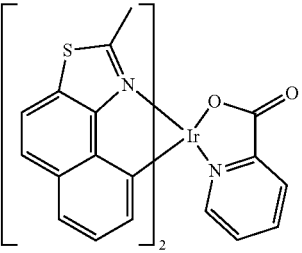 | pseudo fac | 532-538 |
| 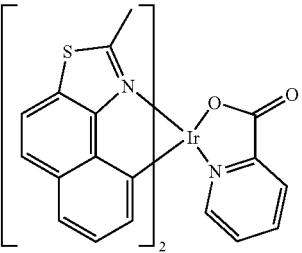 | pseudo mer | 559-565 |

TABLE 3

Estimated emission wavelength of complexes of compounds according to structure I with ring C being mono-substituted:

| Structure | Isomer | Emission [nm] |
|---|---|---|
| 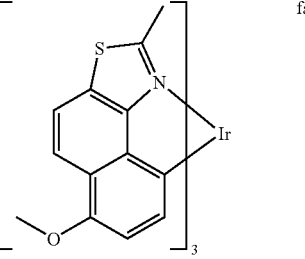 | fac | 587-591 |
| 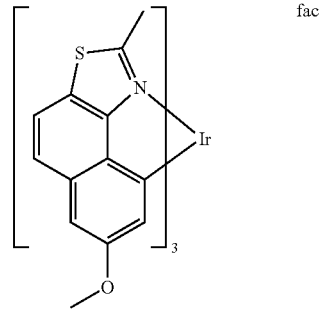 | fac | 538-542 |
| 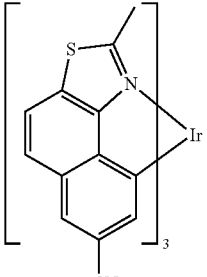 | fac | 530-534 |
| 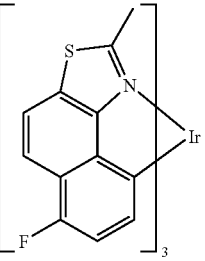 | fac | 567-571 |
| 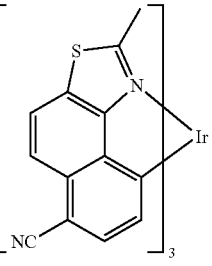 | fac | 542-546 |

TABLE 4

Estimated emission wavelength of complexes of compounds according to structure I with ring B being mono-substituted:

| Structure | Isomer | Emission [nm] |
|---|---|---|
| 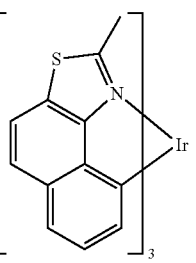 | fac | 541-545 |

TABLE 4-continued

Estimated emission wavelength of complexes of compounds according to structure I with ring B being mono-substituted:

| Structure | Isomer | Emission [nm] |
|---|---|---|
| 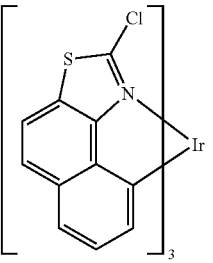 | fac | 547-550 |
| 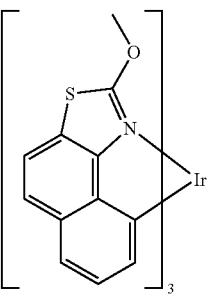 | fac | 537-541 |
| 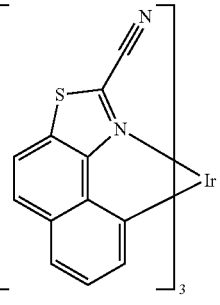 | fac | 627-631 |
| 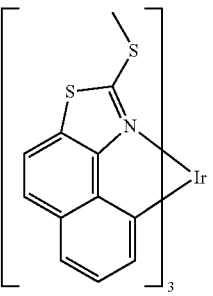 | fac | 587-591 |

TABLE 5

Estimated emission wavelength of complexes of compounds according to structure I with rings A and C both being substituted:

| Structure | Isomer | Emission [nm] |
|---|---|---|
| 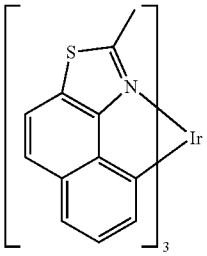 | fac | 541-545 |
| 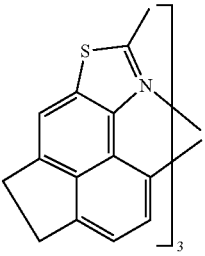 | fac | 559-563 |
| 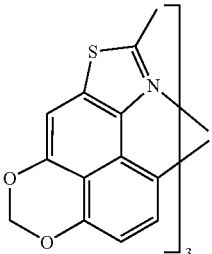 | fac | 571-575 |
| 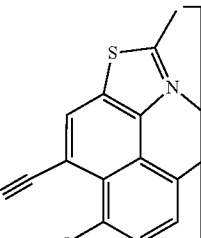 | fac | 671-675 |

Figure 8:
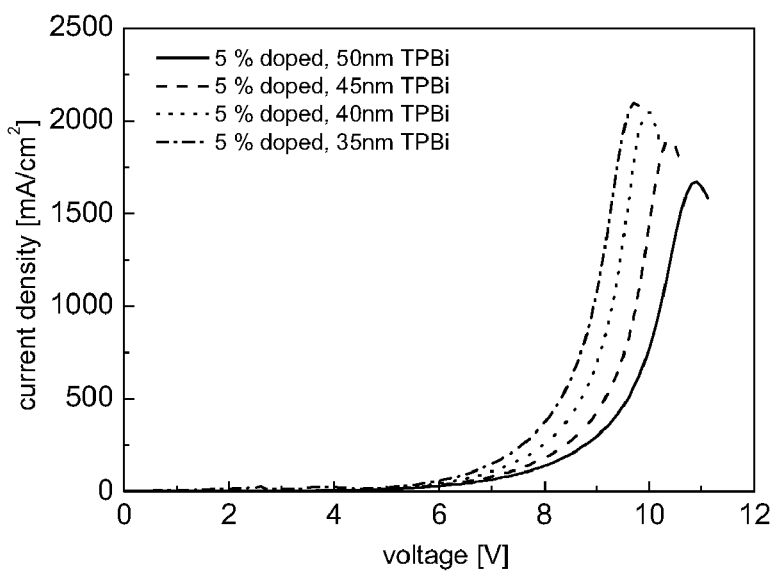
Figure 9:
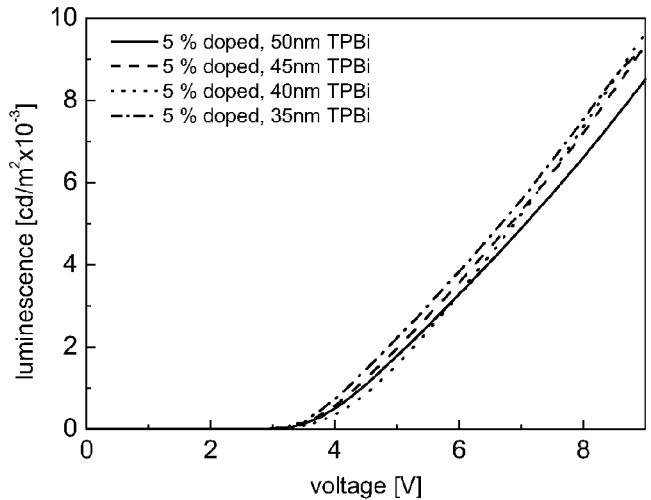
Figure 10:
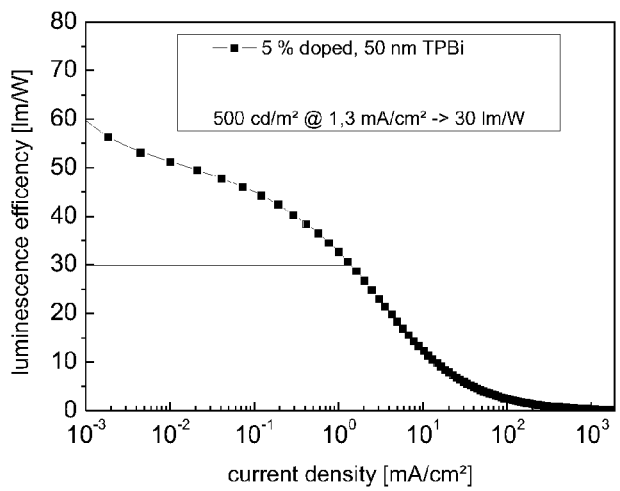

Efficiency measurements of OLEDs according to FIG. 3 are shown in FIGS. 8 to 10, demonstrating the high efficiency obtainable with the compounds of the invention.

Figure 11:
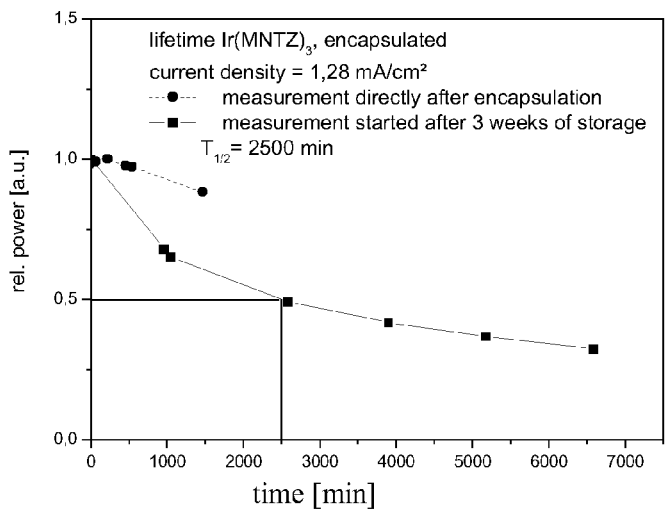
Figure 12:
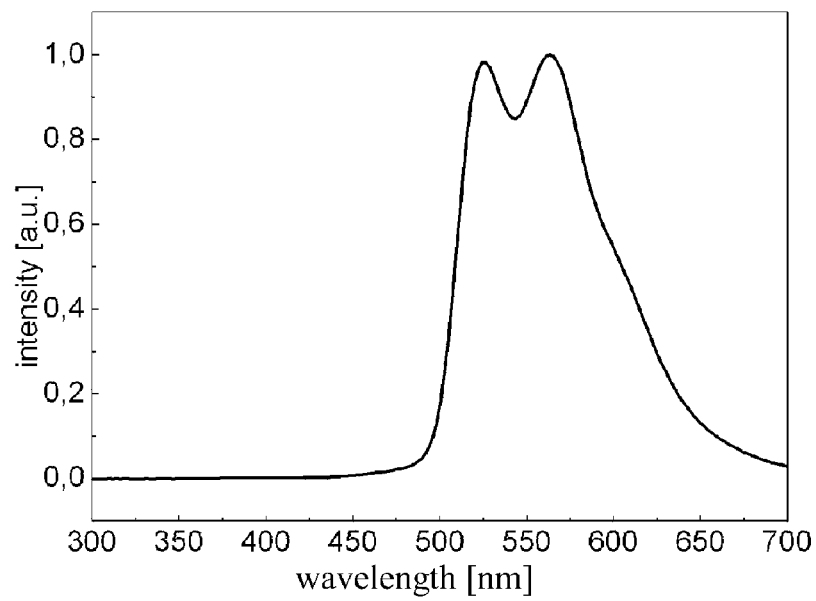

The high long-term stability of the compounds of the invention is demonstrated by the results shown in FIG. 11. An electroluminescence spectrum of Ir(MNTZ)$_3$ is shown FIG. 12.

Figure 13:
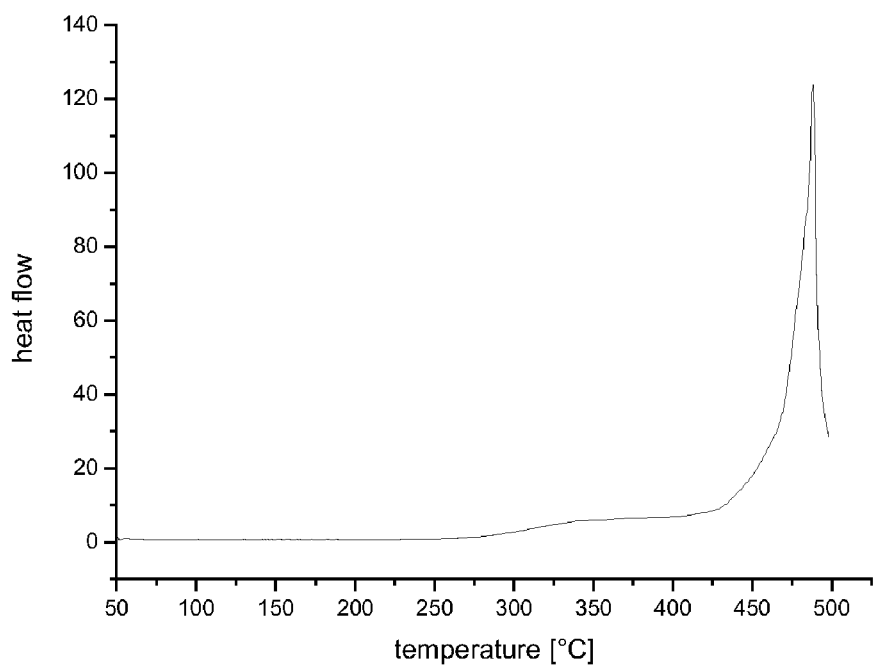
Figure 14:
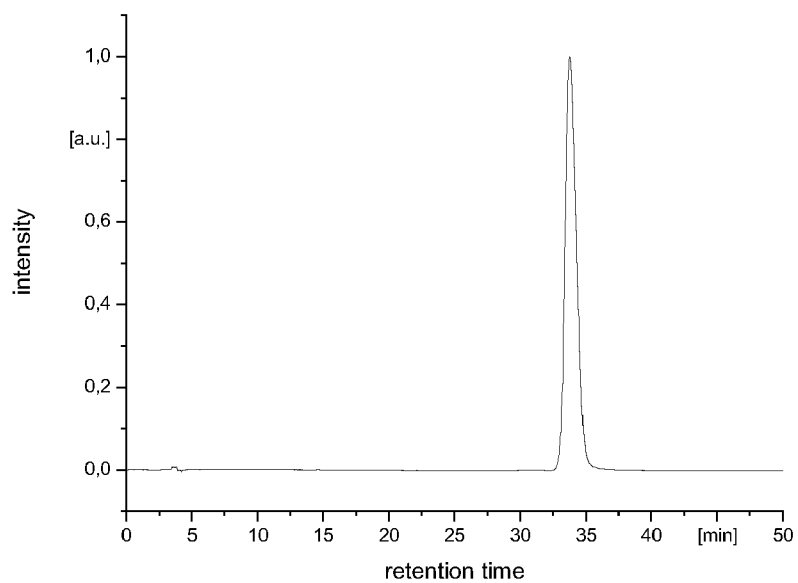
Figure 15:
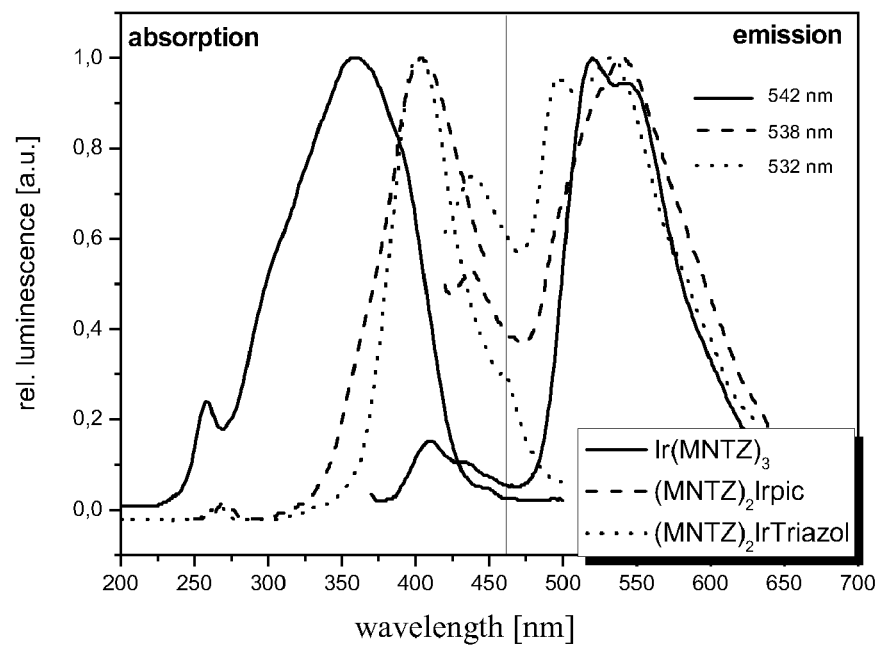
Figure 16:
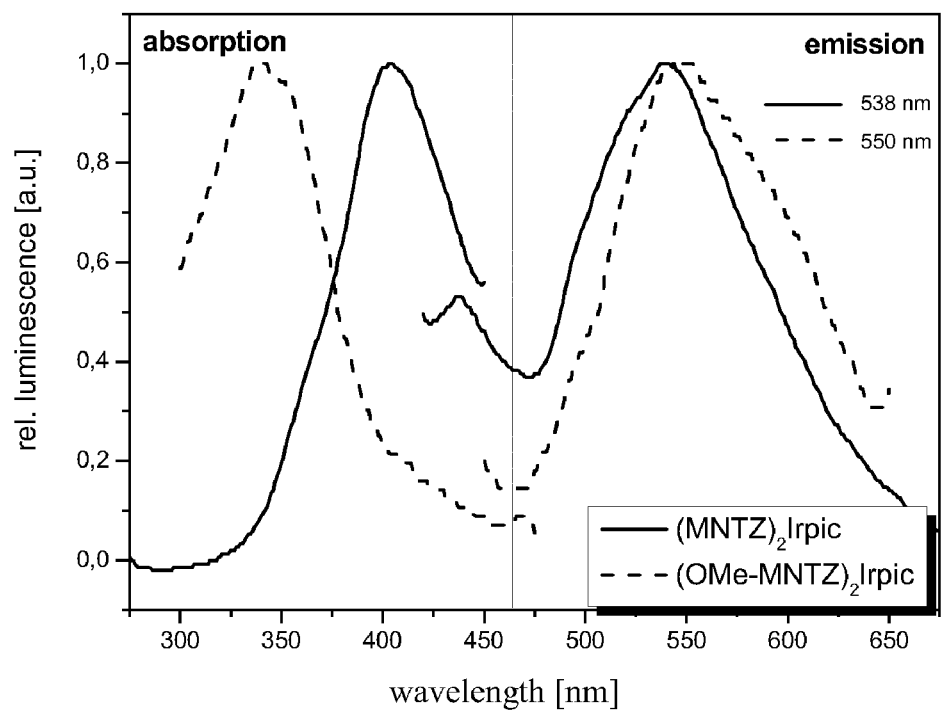

FIG. 13 shows a differential scanning calorimetry (DSC) measurement, demonstrating a very high temperature stability with a remarkably high melting point of 480° C. without decomposition, and the HPLC chromatogramm shown in FIG. 14 of the compounds synthesized and purified according to Example 1 demonstrates the high purity obtainable without extensive purification procedures.

Figures show the emission of compounds of the invention, demonstrating the shift of the emission wavelengths obtained by introduction of heteroatoms and/or of substituents.

The invention claimed is:
1. A compound of formula II

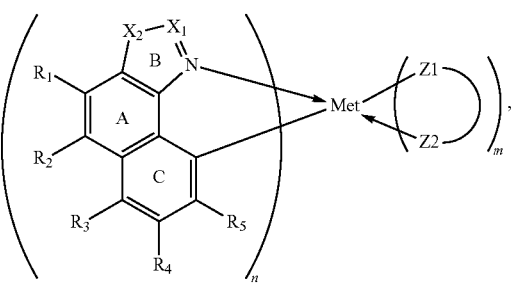

wherein
X1 is CR', wherein R' is selected from the group consisting of A1, CN, NA1A2, OA1, SA1, F, Cl, Br, I, $SO_2A1$, CNO, NCO, CA10, and COOA1 wherein A1 and A2 are selected from the group consisting of substituted(hetero)alkyl, (hetero)aryl and H,
X2 is selected from the group consisting of NR' and S, wherein R' is selected from the group consisting of (hetero)alkyl, (hetero)aryl or H,
R1 to R5 are independently selected from the group consisting of A1, CN, NA1A2, OA1, SA1, F, Cl, Br, I, $SO_2A1$, CNO, NCO, CA10, and COOA1 wherein A1 and A2 are selected from the group consisting of substituted (hetero)alkyl, (hetero)aryl and H,
the metal atom is selected from the group consisting of Pt, Os and Ir,
n is 1 to 3 and m is 3-n for Ir and Os,
n is 1 to 2 and m is 2-n for Pt as the metal atom,
and

is a mono-anionic saturating ligand.
2. An oligomer, dendrimer or polymer comprising at least two compounds according to claim 1 as moieties.
3. A triplet emitter, comprising at least one compound according to claim 1.
4. A process for producing the compound of claim 1, comprising synthesizing said compound in the presence of an intermediate μ-halogeno-complex, wherein the halogen is chlorine or bromine.
5. A process for producing an electrooptic device, comprising applying the compound according to claim 1 to a substrate.
6. The process of claim 5, wherein the compound is applied by coating from solution or sputtering.
7. The process of claim 6, wherein the coating is spray, spin, dip or knife coating or printing.
8. The process of claim 5, wherein at least one organic layer and a final contacting electrode of the device are formed under vacuum.
9. The process of claim 8, wherein a vacuum process is a PVD (physical vapour deposition), CVD (chemical vapour deposition), or an OVPD (organic vapour phase deposition) process.
10. An electrooptical device comprising the compound of claim 1.
11. The electrooptical device of claim 10, wherein the electrooptical device is an OLED, OFET, laser or photovoltaic device.
12. The compound of claim 1, wherein A1 and A2 are selected from the group consisting of substituted (hetero)alkyl and (hetero)aryl carrying a polymerizable group selected from the group consisting of aldehyde, alcohol, cyanato, isocyanato, an at least mono-unsaturated olefinic group, vinyl, alkylidene, allyl, oxethane, acryl, amine, oxirane, carbonic acid and ester groups.
13. The compound of claim 1, wherein cyclic structures A, B and C are substituted with charge transport moieties.
14. The compound of claim 1, wherein
Z1 and Z2 represent atoms which are linked by a chemical bond or by an intermediary group that arranges one, two or three additional atoms between Z1 and Z2,
Z1 and Z2 are independently selected from the group consisting of methylene, substituted methylene, N, NR1, S, O, Se, Te, CR1, SiR1, CR1R2, SiR1R2, CR2=CR3, N=N, CR1=N, R1 to R3 are independently selected from the group consisting of A1, CN, NA1A2, OA1, SA1, F, Cl, Br, I, $SO_2A1$, CNO, NCO, CA1O, and COOA1, and
A1 and A2 are selected from the group consisting of substituted (hetero)alkyl, (hetero)aryl, carrying a polymerizable group, and H.
15. The compound of claim 1, wherein the mono-anionic saturating ligand

represents a moiety selected from the group consisting of acetylacetonate, 2-pyridylacetate, dipivaloylmethanate, 2 pyridylformate, and 2-(4H-[1,2,4]triazol-3-yl)pyridine as a subunit.
16. The compound of claim 1, wherein:
the (hetero)alkyl is selected from the group consisting of linear, branched and cyclic hydrocarbons having 1 to 18 carbon atoms; and
the (hetero)aryl is selected from the group consisting of mono-, bi- and polyunsaturated linear, branched and cyclic hydrocarbons having 1 to 18 carbon atoms.
17. The compound of claim 14, wherein the polymerizable group is selected from the group consisting of aldehyde, alcohol, cyanato, isocyanato, an at least mono-unsaturated olefinic group, vinyl, alkylidene, allyl, oxethane, acryl, amine, oxirane, carbonic acid or ester groups.
18. The compound of claim 17, wherein the polymerizable group is linked to at least one polymeric group selected from the group consisting of polyalkylene groups, matrix groups, electron transporting groups and hole transporting groups.

* * * * *